US012263295B2

(12) United States Patent
Cook

(10) Patent No.: US 12,263,295 B2
(45) Date of Patent: Apr. 1, 2025

(54) DEVICE FOR DISPENSING MEDICATION FOR MEDICAL TREATMENT

(71) Applicant: Migraine Solutions, LLC, Asheville, NC (US)

(72) Inventor: Jason Cook, Asheville, NC (US)

(*) Notice: Subject to any disclaimer, the term of this patent is extended or adjusted under 35 U.S.C. 154(b) by 774 days.

(21) Appl. No.: 16/863,987

(22) Filed: Apr. 30, 2020

(65) Prior Publication Data
US 2021/0338946 A1    Nov. 4, 2021

(51) Int. Cl.
*A61M 11/00* (2006.01)
*A61M 11/02* (2006.01)

(52) U.S. Cl.
CPC ........... *A61M 11/007* (2014.02); *A61M 11/02* (2013.01); *A61M 2202/048* (2013.01); *A61M 2210/0618* (2013.01)

(58) Field of Classification Search
CPC .... A61M 5/3159–31593; A61M 15/08; A61M 5/1452; A61M 5/1456; A61M 5/14566; A61M 11/06; A61M 15/0028; A61M 2205/073; A61M 2210/0618; A61M 2202/048; A61M 19/00; A61M 11/007; A61M 11/02; A61M 15/0021; A61M 2202/0241; A61M 2205/276
See application file for complete search history.

(56) References Cited

U.S. PATENT DOCUMENTS

| | | | | |
|---|---|---|---|---|
| 5,582,598 | A * | 12/1996 | Chanoch | A61M 5/31585 604/218 |
| 2005/0281751 | A1* | 12/2005 | Levin | A61K 31/00 424/45 |
| 2017/0165430 | A1* | 6/2017 | Holtwick | A61M 5/31556 |
| 2017/0239422 | A1* | 8/2017 | Kodgule | A61P 31/12 |
| 2018/0256867 | A1* | 9/2018 | Levin | A61M 15/08 |

OTHER PUBLICATIONS

Nasacort.com, Instruction of Use, archived Jan. 24, 2017, https://web.archive.org/web/20170124190539/https://www.nasacort.ca/en/how-to-use; accessed Aug. 11, 2022 (Year: 2017).*

* cited by examiner

*Primary Examiner* — Elliot S Ruddie

(57) ABSTRACT

The device for dispensing medication for migraine treatment may comprise a medication applicator, an activator, and a safety interlock. The medication applicator may store a medication and may dispense the medication as an aerosol mist. The medication applicator may be adapted to dispense the medication through a nostril of a user directed at a sphenopalatine ganglion. The activator may be operable to release the medication in two doses—a first dose may be dispensed upon the activation of a first button and a second dose may be dispensed upon the activation of a second button. The safety interlock may prevent premature dispensing of the medication and may constrain dispensing such that the first dose must be dispensed before the second dose. The invention may be adapted for the user to self-administer the medication while the user is upright.

15 Claims, 8 Drawing Sheets

DEVICE FOR DISPENSING MEDICATION FOR MEDICAL TREATMENT

CROSS-REFERENCE TO RELATED APPLICATION

This application is a continuation-in-part of U.S. application Ser. No. 16/533,391, filed Aug. 6, 2019 and entitled "Drug Delivery System".

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

The application of a local anesthetic, such as lidocaine, to the sphenopalatine ganglion (SPG) can be effective in reducing the pain associated with migraines. This has been historically accomplished through the use of a cotton swab applicator saturated in viscous local anesthetic and applied intranasally while the migraine sufferer lies in a supine position. However, this method requires the assistance or supervision of a trained medical professional.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

Figure 1:
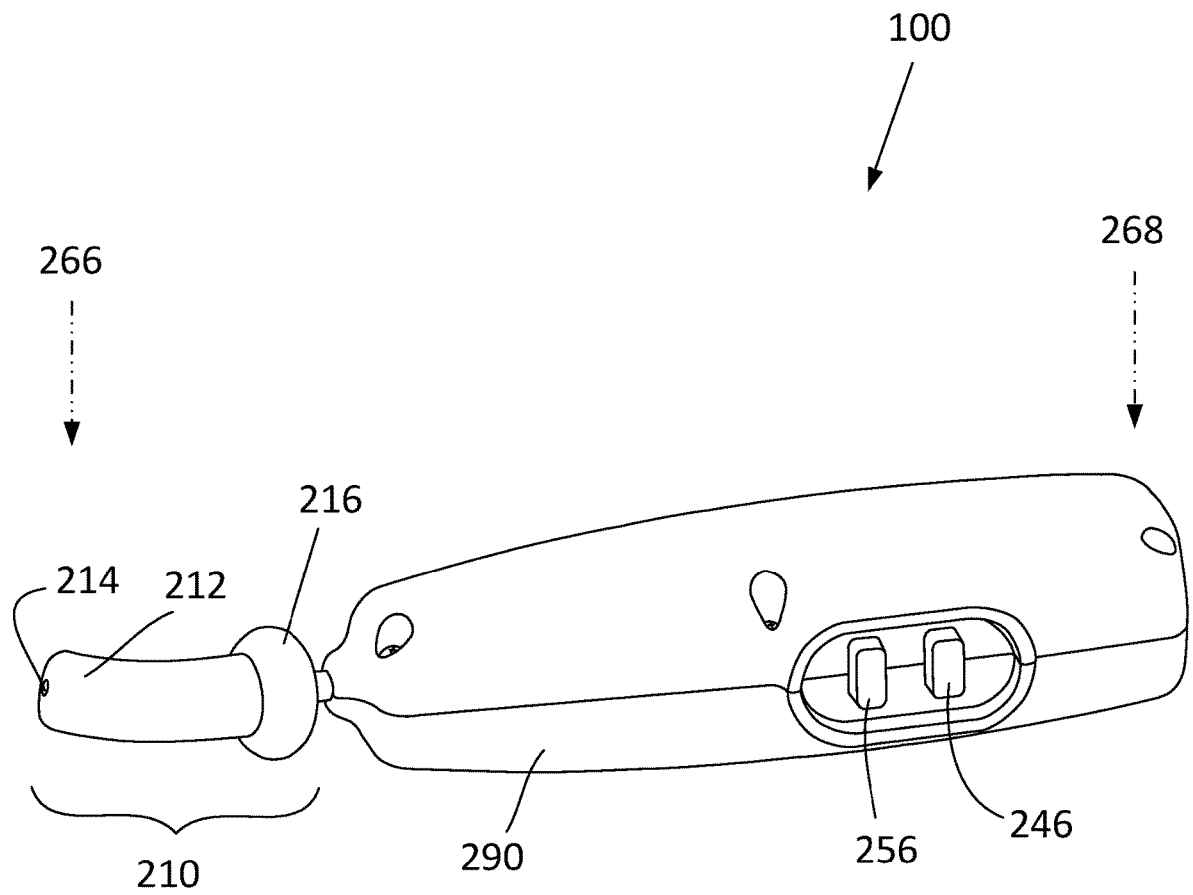
FIG. 1 is an isometric view of the device consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The device for dispensing medication for migraine treatment (hereinafter invention) may comprise a medication applicator, an activator, and a safety interlock. The medication applicator may store a medication and may dispense the medication as an aerosol mist. The medication applicator may be adapted to dispense the medication through a nostril of a user directed at a sphenopalatine ganglion. The activator may be operable to release the medication in two doses. A first dose may be dispensed upon the activation of a first button. A second dose may be dispensed upon the activation of a second button. The safety interlock may prevent premature dispensing of the medication. The safety interlock may constrain dispensing such that the first dose must be dispensed before the second dose. The invention may be adapted for the user to self-administer the medication. The invention may be adapted to dispense the medication while the user is upright. As non-limiting examples, the user may be sitting or standing while using the invention.

Throughout this document, proximal refers to a direction closer to the nostril and distal refers to a direction that is opposite proximal.

The medication applicator may comprise a cartridge, a nozzle, a seal, and a plunger. The medication applicator may dispense the aerosol mist comprising the medication through the nozzle when the plunger pushes the seal towards a proximal end of the cartridge.

The cartridge may be a tubular container for the medication. The cartridge may comprise a nozzle interface, a proximal cartridge aperture, and a distal cartridge aperture. The nozzle interface may be a coupler for accepting the nozzle and may be located on the proximal end of the cartridge. The medication may be forced from within the cartridge through the proximal cartridge aperture which may be located at the center of the nozzle interface. The distal cartridge aperture may be located at a distal end of the cartridge. The seal may slidably interface with the distal cartridge aperture.

In some embodiments, the medication may be a liquid anesthetic. In a preferred embodiments, the medication may be a 4% lidocaine solution.

The nozzle may be adapted to direct the medication from the cartridge to the nostril of the user. The nozzle may be tubular and may comprise a bend of between 5.0 to 60.0 degrees (inclusive) at a midpoint of the tube. The length of the nozzle may be selected to assure that one or more apertures located at the proximal end of the atomizer are positioned beyond the inferior turbinate when the nozzle is inserted into a nostril. The nozzle may comprise an atomizer, an insertion limiter, and a cartridge interface. The atomizer may be located at the proximal end of the nozzle. The atomizer may convert the medication into the aerosol mist as the medication is forced through the one or more apertures under pressure. The pressure may result from proximal movement of the seal within the cartridge during activation. The atomizer may be blunt to avert nasal trauma. The insertion limiter may be a flange located at the proximal end of the nozzle and axially surrounding the nozzle. The insertion limiter may limit the insertion distance of the nozzle into the nostril. The cartridge interface may mate with the nozzle interface on the cartridge. The medication forced from the cartridge may enter the nozzle via a nozzle aperture in the cartridge interface.

The seal may be a semi-rigid plug that slidably couples to the interior of the cartridge at the distal end of the cartridge. The outer diameter of the seal may match the inner diameter of the cartridge such that the medication is prevent from escaping the cartridge via the distal end of the cartridge. Forward motion of the seal within the cartridge may pressurize the medication and may force the medication out of the cartridge via the proximal cartridge aperture. The seal may be moved proximally in steps such that the medication is dispensed in multiple doses.

The plunger may move the seal in a proximal direction when a dispensing force is applied to the plunger. The plunger may comprise a seal interface at the proximal end of the plunger. The seal interface may mate with the seal such that movement of the plunger is conveyed to the seal. The plunger may comprise a thrust ring. A spring may apply the dispensing force to the plunger my pressing against the thrust ring.

The activator may be operable to apply the dispensing force such that the plunger may move in a proximal direction to dispense the medication through the nozzle. The activator may comprise the spring, a first retainer, and a second retainer. The spring may be a compression spring. The spring may be compressed between the thrust ring of the plunger and the interior distal end of a housing.

Initially, proximal movement of the plunger may be prevented by interference between the plunger and the first retainer. Activating the first button may move the first retainer laterally, may eliminate the interference between the plunger and the first retainer, and may allow the plunger to move proximally, thus dispensing the first dose of the medication. Proximal movement of the plunger may then be prevented by interference between the plunger and the second retainer. Activating the second button may move the second retainer laterally, may eliminate the interference between the plunger and the second retainer, and may allow the plunger to move proximally, thus dispensing the second dose of the medication.

The first retainer may comprise the first button, a first retainer extension, a first stopping ring, and a retainer interference arm. The first retainer may be an armature that may slide laterally within the housing between a first button locked position and a first button unlocked position. When the first retainer is in the first button locked position, the first stopping ring may interfere with the thrust ring of the plunger and may prevent proximal movement of the plunger. When the first retainer is in the first button unlocked position, the plunger may slide past the first retainer. The first button may be exposed on the exterior of the housing. The first retainer may slide from the first button locked position to the first button unlocked position when the first button is activated. The first retainer extension may prevent the first retainer from moving into the first button unlocked position if the safety interlock is set to restrict dispensing of the first dose. The retainer interference arm may enforce sequencing of the first dose and the second dose by preventing the safety interlock from moving to a position that would permit dispensing the second dose unless the first dose has been dispensed.

The second retainer may comprise the second button, a second retainer extension, and a second stopping ring. The second retainer may be an armature that may slide laterally within the housing between a second button locked position and a second button unlocked position. When the second retainer is in the second button locked position, the second stopping ring may interfere with the thrust ring of the plunger and may prevent proximal movement of the plunger. When the second retainer is in the second button unlocked position, the plunger may slide past the second retainer. The second button may be exposed on the exterior of the housing. The second retainer may slide from the second button locked position to the second button unlocked position when the second button is activated. The second retainer extension may prevent the second retainer from moving into the second button unlocked position if the safety interlock is set to restrict dispensing of the second dose.

The safety interlock may be a three-position interlock that may prevent the first dose of the medication from being dispensed prematurely and may prevent the second dose of the medication from being dispensed simultaneously with the first dose. The safety interlock may prevent the first dose and the second dose from being dispensed when in a first safety lock position. The safety interlock may permit the first dose only to be dispensed when in a second safety lock position. The safety interlock may permit the second dose to be dispensed when in a third safety lock position. The safety interlock may not be moved from the second safety lock position to the third safety lock position until the first dose has been dispensed.

The safety interlock may comprise a lock base, a slide handle, and a lock interference arm. When the lock base is in the first safety lock position, the lock base may block movement of the first retainer to the first button unlocked position and may block movement of the second retainer to the second button unlocked position. Movement of the first retainer and the second retainer may be blocked by interference between the lock base and the first retainer extension on the first retainer and between the lock base and the second retainer extension on the second retainer.

When the lock base is in the second safety lock position, the lock base may allow movement of the first retainer to the first button unlocked position and may block movement of the second retainer to the second button unlocked position. Movement of the first retainer may be allowed by clearance for the first retainer extension to move into a notch on the lock base. Movement of the second retainer may be blocked by interference between the lock base and the second retainer extension on the second retainer.

When the lock base is in the third safety lock position, the lock base may allow movement of the second retainer to the second button unlocked position. Movement of the second retainer may be allowed by clearance for the second retainer extension to move past the lock base. The slide handle may be operable to slide the lock base between the first safety lock position, the second safety lock position, and the third safety lock position. The slide handle may be accessible on the exterior of the housing. The lock base may comprise the notch.

The lock interference arm may be a protrusion of the lock base that prevents the lock base from moving to the third safety lock position unless the first retainer has been moved to the first button unlocked position during the dispensing of the first dose. Movement of the lock base to the third safety lock position may be prevented by interference between the lock interference arm and the retainer interference arm on the first retainer. When the first retainer is moved to the first button unlocked position, the retainer interference arm moves clear of the lock interference arm and the lock interference arm may then move past the retainer interference arm when the lock base moves to the third safety lock position.

The housing may be an enclosure for the cartridge, the activator, and the safety interlock. In some embodiments, the housing may comprise an upper housing and a lower housing held together by a plurality of fasteners. In some embodiments, the housing may be configured to allow an end cap located at the distal end of the housing to be removed for access to the interior of the housing.

The first dose may be dispensed with the nozzle inserted into a first nostril and the second dose may be dispensed with the nozzle inserted into a second nostril. As a non-limiting example, the first nostril may be the left nostril and the second nostril may be the right nostril, or vice versa. The capacity of the cartridge may be selected such that both doses may be dispensed into a single nostril without harm. As a non-limiting example, the cartridge may have a capacity of 0.6 ml. The invention may dispense 0.3 ml when the first button is pressed. The invention may dispense 0.3 ml when the second button is pressed.

In use, the invention may be preloaded with a medication and a safety interlock may prevent the medication from being dispensed. When the safety interlock is in a first safety lock position, neither a first button nor a second button may be pressed and therefore neither a first dose nor a second dose may be dispensed.

The safety interlock may be moved to a second safety lock position, an atomizer may be placed within a first nostril until an insertion limiter is against the entrance to the first nostril, and the first button may be pressed to dispense the first dose. The safety interlock may be moved to a third safety lock position, the atomizer may be placed within a second nostril until the insertion limiter is against the entrance to the second nostril, and the second button may be pressed to dispense the second dose. The safety interlock may be restricted from moving to the third safety lock position until the first button has been activated to dispense the first dose.

The medication may be self-administered by a user by virtue of the fact that the first dose and the second dose may comprise predetermined dosages of the medication that have been preloaded into a cartridge and the first dose and the second dose may be individually dispensed by the user via an activator. The medication may be dispensed while the user is in an upright position by virtue of the fact that the medication is dispensed into a nostril as an aerosol mist and the aerosol mist may reach the nasal cavity adjacent to a sphenopalatine ganglion.

Turning now to FIG. 1, the figure shows an isometric view of the invention 100 and denotes the proximal end 266 and the distal end 268. In an exemplary embodiment, the nozzle 210 is shown extending from the housing 290 at the proximal end 266 of the housing 290. The proximal end 266 of the nozzle 210 terminates with the atomizer 212. The atomizer 212 comprises the insertion limiter 216 to limit insertion distance. The atomizer 212 may discharge the medication via the one or more apertures 214. Pushing the first button 246 may dispense the first dose of the medication via the atomizer 212. Pushing the second button 256 may dispense the second dose of the medication via the atomizer 212.

Figure 2:
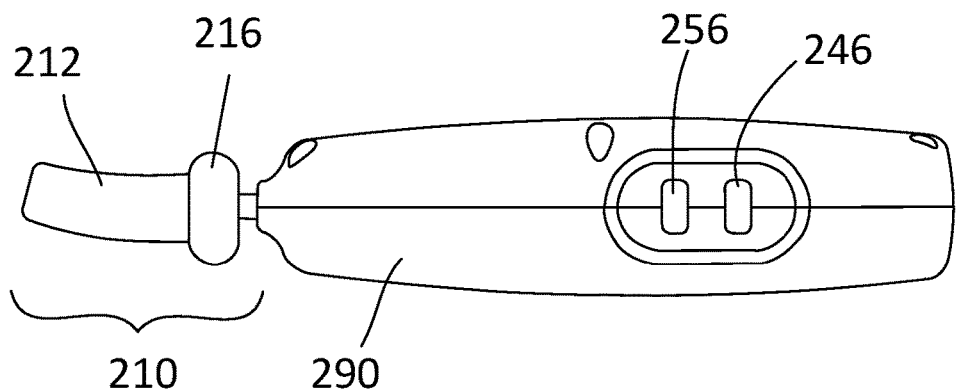
FIG. 2 is a right side view of the device consistent with certain embodiments of the present invention.

Turning now to FIG. 2, the figure shows a right side view of the device. In an exemplary embodiment, the nozzle 210 is shown extending from the housing 290. The insertion limiter 216 may limit insertion distance of the nozzle 210. Pushing the first button 246 may dispense the first dose of the medication via the atomizer 212. Pushing the second button 256 may dispense the second dose of the medication via the atomizer 212.

Figure 3:
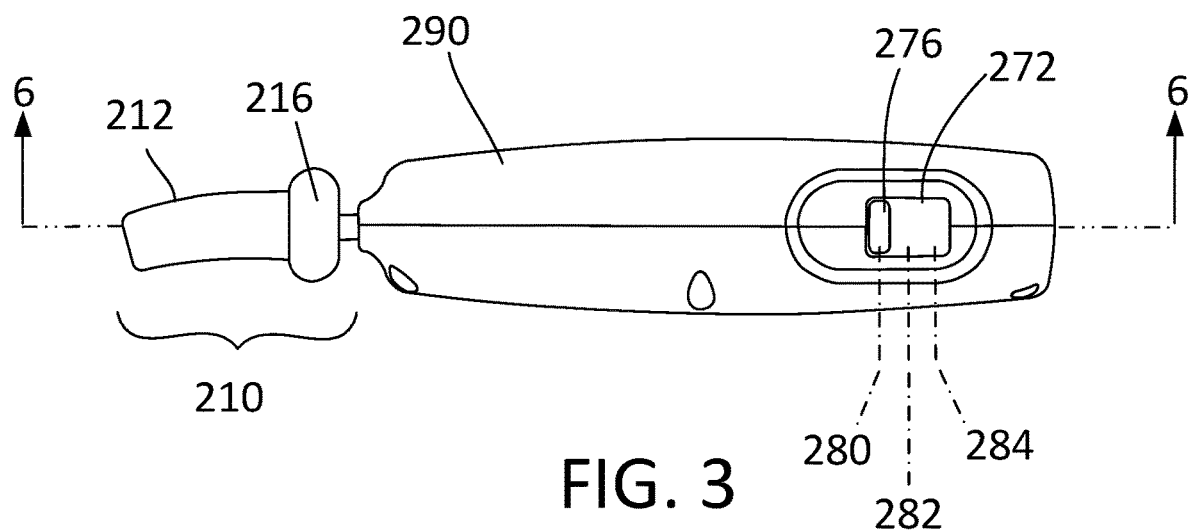
FIG. 3 is a left side view of the device consistent with certain embodiments of the present invention.

Turning now to FIG. 3, the figure shows a left side view of the device. Note that the unit is shown inverted in FIG. 3, as compared to FIG. 2. In an exemplary embodiment, the medication may be dispensed though the nozzle 210 via the atomizer 212. The insertion limiter 216 may limit insertion distance of the nozzle 210. The slide handle 276 of the safety interlock may be accessible on the exterior of the housing 290. The slide handle 276 may be moved from the first safety lock position 280 to the second safety lock position 282 and to the third safety lock position 284. The slide handle 276 may move the lock base 272 of the safety interlock as the slide handle 276 is moved. The safety interlock may prevent the first dose and the second dose from being dispensed when in the first safety lock position 280. The safety interlock may permit the first dose only to be dispensed when in the second safety lock position 282. The safety interlock may permit the second dose to be dispensed when in the third safety lock position 284. The safety interlock may not be moved from the second safety lock position 282 to the third safety lock position 284 until the first dose has been dispensed.

Figure 4:
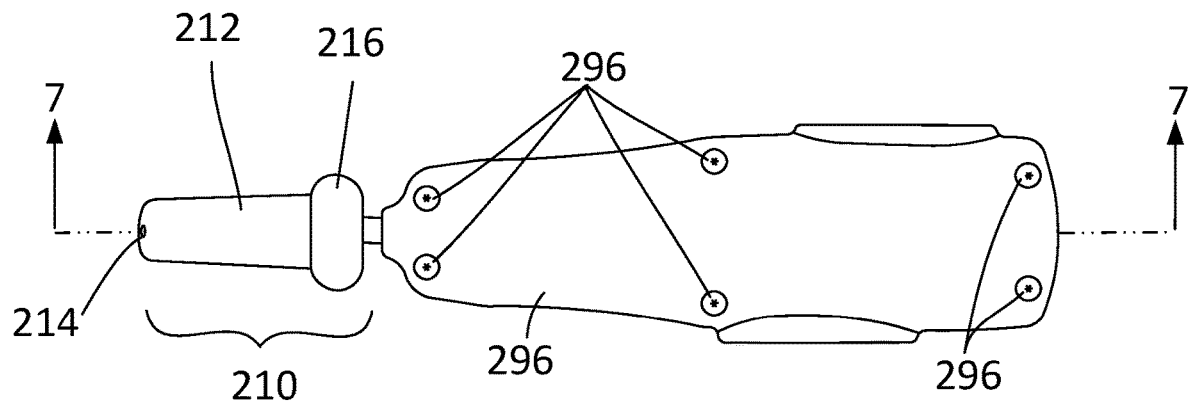
FIG. 4 is a top view of the device consistent with certain embodiments of the present invention.

Turning now to FIG. 4, the figure shows a top view of the device. In an exemplary embodiment, the housing 290 may be held closed by the plurality of fasteners 296. The one or more apertures 214 are shown on the atomizer 212 at the termination of the nozzle 210. The insertion limiter 216 may limit insertion distance of the nozzle 210.

Figure 5:
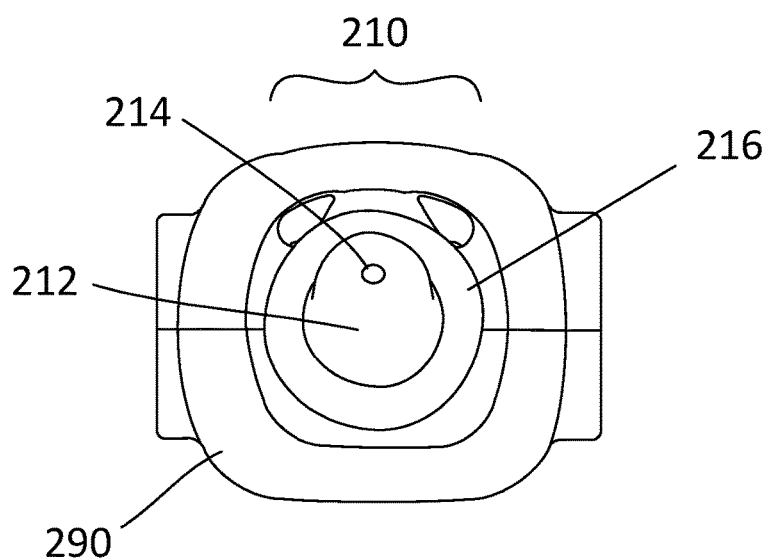
FIG. 5 is a front view of the device consistent with certain embodiments of the present invention.

Turning now to FIG. 5, the figure shows a front view of the device. As an exemplary embodiment, the nozzle 210 with the insertion limiter 216, the atomizer 212, and the one or more apertures 214 are illustrated, along with the housing 290.

Figure 6:
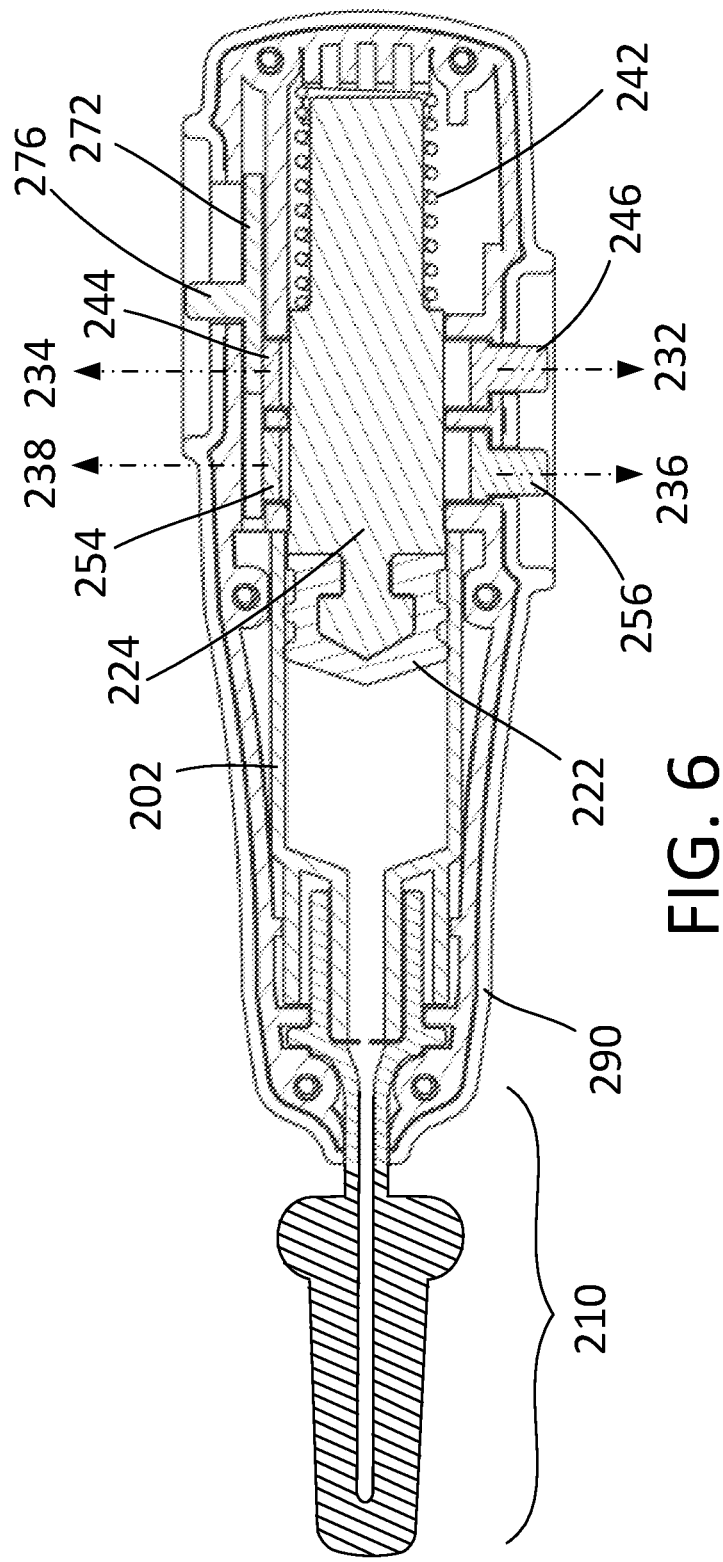
FIG. 6 is a cross-sectional view of the device across 6-6 as shown in FIG. 3 consistent with certain embodiments of the present invention.

Turning now to FIG. 6, the figure shows a cross-sectional view of an embodiment of the disclosure across 6-6 as shown in FIG. 3. In an exemplary embodiment, the cartridge 202 may store the medication and may dispense the medication via the nozzle 210 when the plunger 224 forces the seal 222 towards the nozzle 210. The plunger 224 may move towards the nozzle 210 in two steps due to force exerted by the spring 242. The plunger 224 may move to dispense the first dose as the first retainer 244 moves out of the way of the plunger 224 when the first button 246 is pressed to move the first retainer 244 from the first button locked position 232 to the first button unlocked position 234. The plunger 224 may move to dispense the second dose as the second retainer 254 moves out of the way of the plunger 224 when the second button 256 is pressed to move the second retainer 254 from the second button locked position 236 to the second button unlocked position 238. The lock base 272 of the safety interlock may prevent the first retainer 244 and/or the second retainer 254 from moving until the lock base 272 is moved distally using the slide handle 276. The housing 290 may enclose and guide the motion of elements of the medication applicator and the safety interlock.

Figure 7:
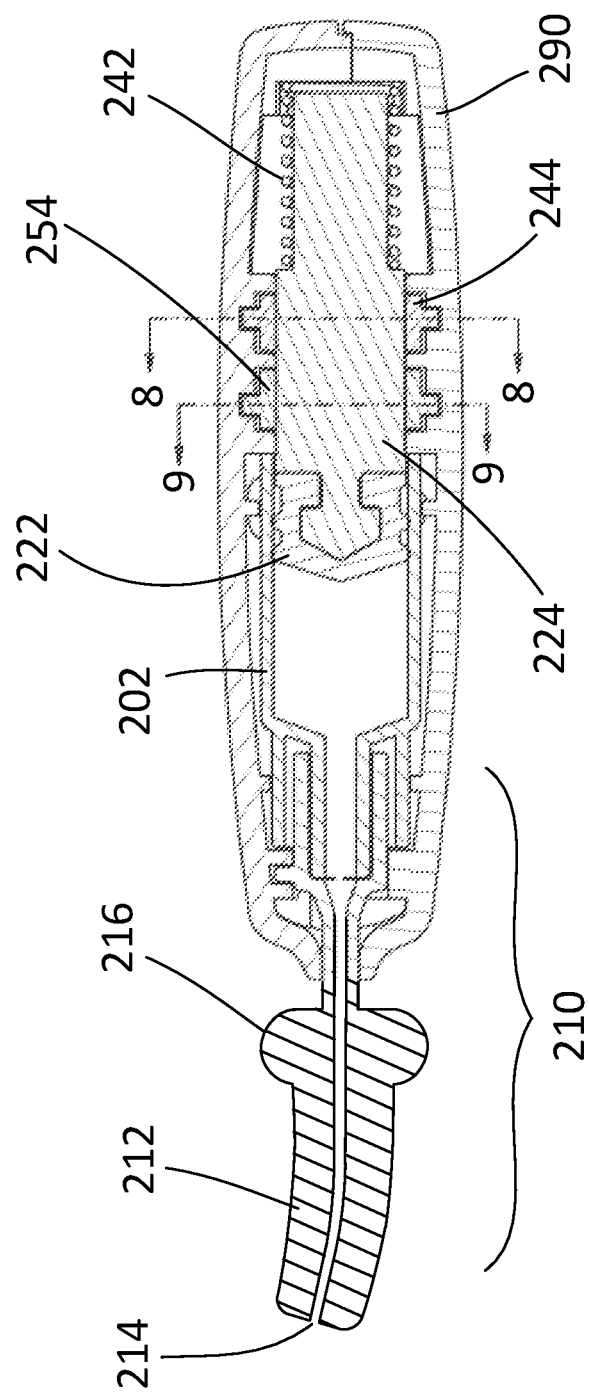
FIG. 7 is a cross-sectional view of the device across 7-7 as shown in FIG. 4 consistent with certain embodiments of the present invention.

Turning now to FIG. 7, the figure shows a cross-sectional view of an embodiment of the disclosure across 7-7 as shown in FIG. 4. In an exemplary embodiment, the cartridge 202 may store the medication and may dispense the medication via the nozzle 210 when the plunger 224 forces the seal 222 towards the nozzle 210. The medication may be dispensed via the one or more apertures 214 of the atomizer 212. The insertion limiter 216 may limit insertion distance of the nozzle 210. The plunger 224 may move towards the nozzle 210 in two steps due to force exerted by the spring 242. The plunger 224 may move to dispense the first dose as the first retainer 244 moves out of the way of the plunger 224 and may move to dispense the second dose as the second retainer 254 moves out of the way of the plunger 224. The housing 290 may enclose and guide the motion of elements of the medication applicator and the safety interlock.

Figure 8:
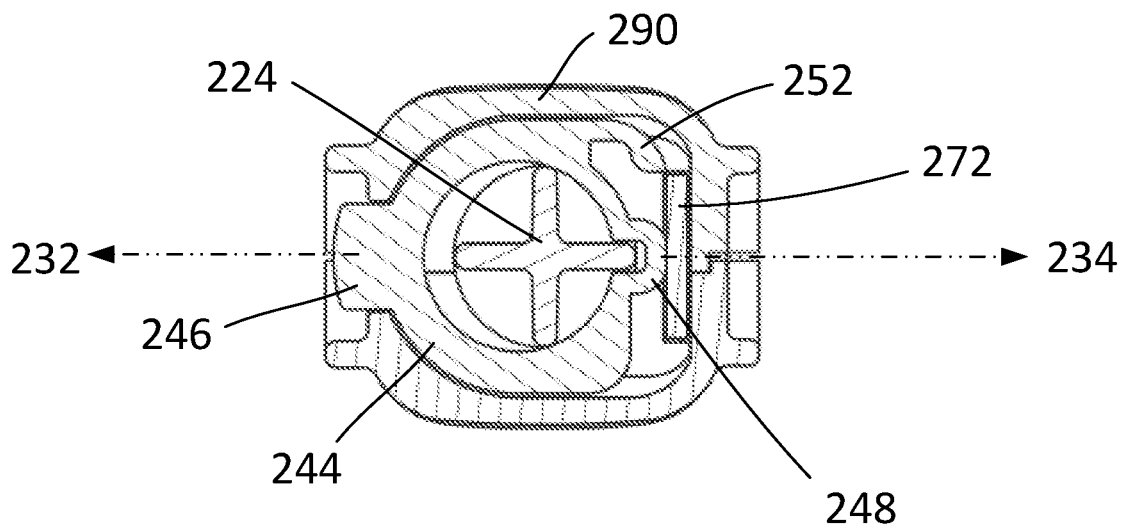
FIG. 8 is a cross-sectional view of the device across 8-8 as shown in FIG. 7 consistent with certain embodiments of the present invention.

Turning now to FIG. 8, the figure shows a cross-sectional view of an embodiment of the disclosure across 8-8 as shown in FIG. 7. In an exemplary embodiment, the plunger 224 is blocked from moving in a proximal direction within the housing 290 by the first retainer 244 which is in the first button locked position 232. The first retainer 244 is prevented from moving to the first button unlocked position 234 by interference between the first retainer extension 248 and the lock base 272 of the safety interlock. By moving the slide handle 276 to the second safety lock position 282 as shown in FIG. 3, the lock base 272 may slide such that the first button 246 may be pressed to move the first retainer 244 to the first button unlocked position 234. The retainer interference arm 252 in FIG. 8 may prevent the lock base 272 from moving the third safety lock position 284 shown in FIG. 3.

Figure 9:
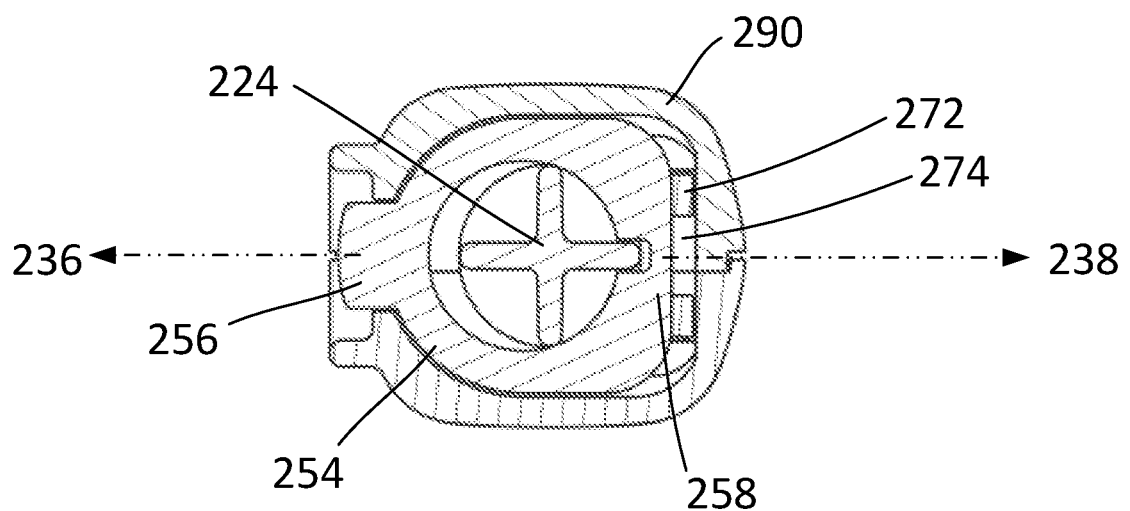
FIG. 9 is a cross-sectional view of the device across 9-9 as shown in FIG. 7 consistent with certain embodiments of the present invention.

Turning now to FIG. 9, the figure shows a cross-sectional view of an embodiment of the disclosure across 9-9 as shown in FIG. 7. In an exemplary embodiment, the plunger 224 is blocked from moving in a proximal direction within the housing 290 by the second retainer 254 which is in the second button locked position 236. The second retainer 254 is prevented from moving to the second button unlocked position 238 by interference between the second retainer extension 258 and the lock base 272 of the safety interlock. By moving the slide handle 276 to the third safety lock position 284 as shown in FIG. 3, the lock base 272 may slide such that the second button 256 may be pressed to move the second retainer 254 to the second button unlocked position 238. FIG. 9 also illustrates the notch 274 in the lock base 272 of the safety interlock which may provide clearance for the first retainer extension 248 of FIG. 8 to move into when the first retainer extension 248 and the notch 274 are aligned.

Figure 10:
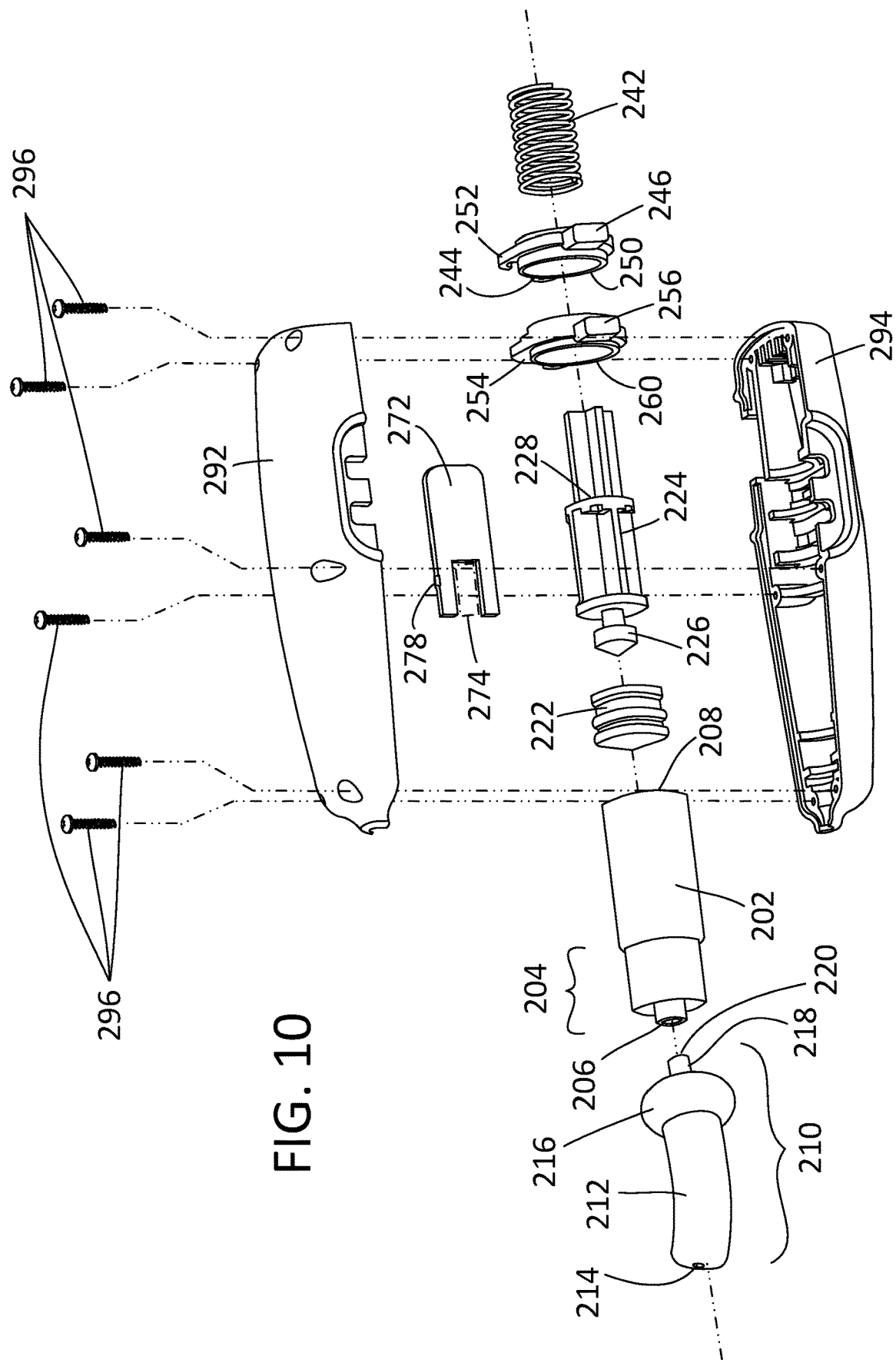
FIG. 10 is an exploded view of the device consistent with certain embodiments of the present invention.
Figure 11:
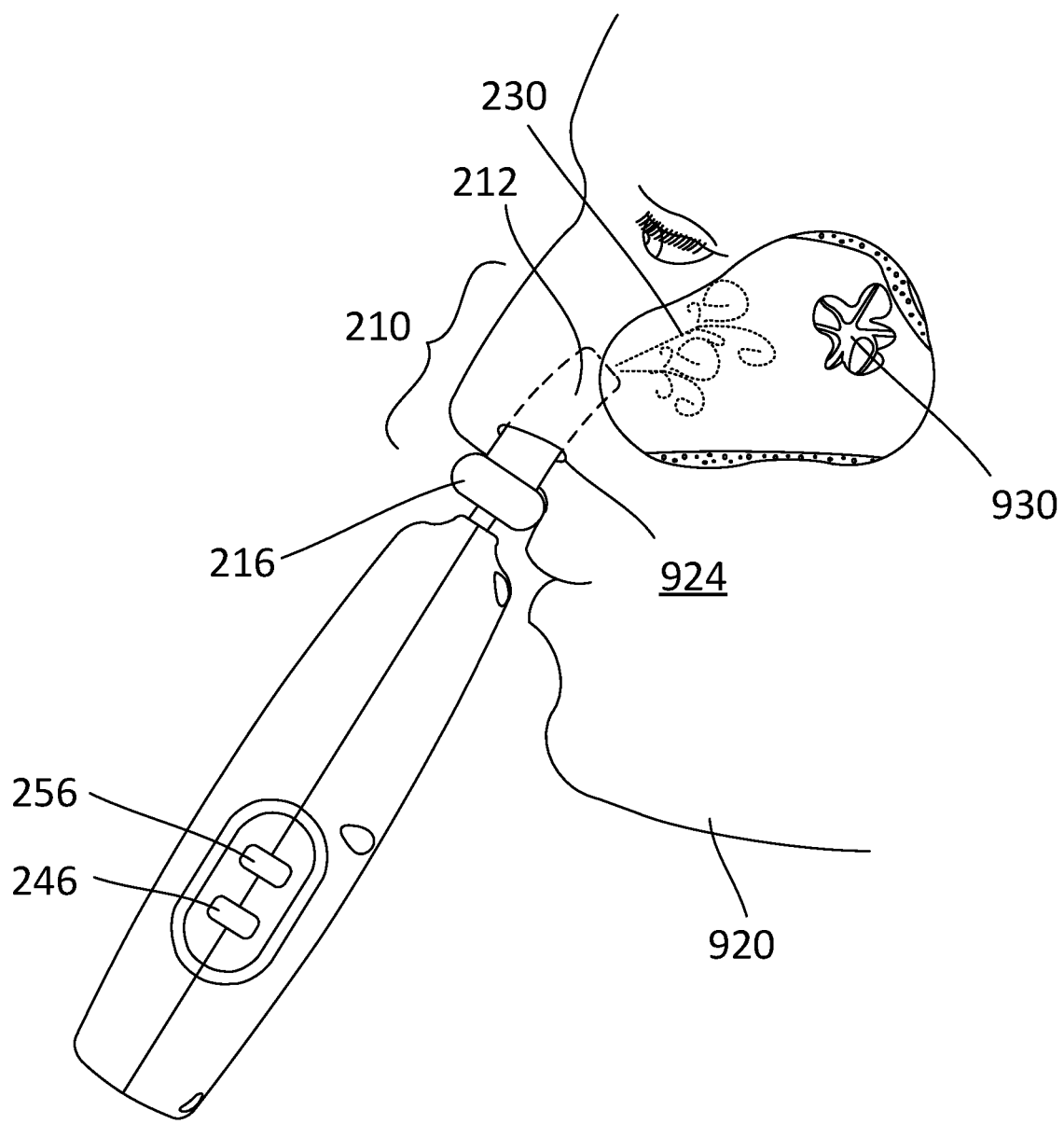
FIG. 11 is an in-use view of the device consistent with certain embodiments of the present invention.

Turning now to FIG. 10, the figure shows an exploded view of an embodiment of the disclosure. In an exemplary embodiment, the nozzle 210 is shown on the left side of the figure. The one or more apertures 214 in the atomizer 212 may disperse the aerosol mist 230. The insertion limiter 216 may limit the distance that the nozzle 210 may be pushed into the first nostril or the second nostril. The cartridge interface 218 may mate with the nozzle interface 204 of the cartridge 202. The medication may pass out of the cartridge 202 through the proximal cartridge aperture 206 into the nozzle aperture 220. The seal 222 may be pushed through the cartridge 202 via the distal cartridge aperture 208 by the plunger 224.

The seal interface 226 of the plunger 224 may couple with the seal 222 to move the seal 222. The plunger 224 may be pushed distally by the spring 242 which may press against the thrust ring 228 of the plunger 224. The plunger 224 may move distally in stages. Initially, the plunger 224 may be constrained by interference between the proximal side of the thrust ring 228 and the distal side of the first stopping ring 250 on the first retainer 244. Once the first button 246 has been pressed, the plunger 224 may advance proximally to dispense the first dose until the plunger 224 is stopped by interference between the proximal side of the thrust ring 228 and the distal side of the second stopping ring 260 on the second retainer 254. When the second button 256 has been pressed, the plunger 224 may advance proximally to dispense the second dose.

The lock base 272 of the safety interlock may control the sequencings of dispersements. Initially, the lock base 272 may prevent pressing either the first button 246 or the second button 256. The lock base 272 may be moved distally to position the notch 274 adjacent to the first retainer 244, allowing the first button 246 to be pressed. The lock base 272 may be moved distally again such that the lock base 272 does not block the second retainer 254, allowing the second button 256 to be pressed. The lock interference arm 278 on the lock base 272 may interfere with the retainer interference arm 252 on the first retainer 244 to prevent moving the lock base 272 to a position that would allow dispensing the second dose if the first dose has not been dispensed.

As a non-limiting example, the device may be housed by the upper housing 292 and the lower housing 294 which may be coupled to each other using the plurality of fasteners 296.

Turning now to FIG. 11, the figure shows the use of an embodiment of the disclosure. In an exemplary embodiment, the user 920 may hold the device with the nozzle 210 inserted into the first nostril or the second nostril such that the insertion limiter 216 of the nozzle 210 is pressed against the nostril 924. Pressing the first button 246 for the first nostril or the second button 256 for the second nostril may result in the aerosol mist 230 being dispersed via the atomizer 212. The aerosol mist 230 may travel through the nasal cavities until the medication is adjacent to the sphenopalatine ganglion 930 and may thus provide relief.

While certain illustrative embodiments have been described, it is evident that many alternatives, modifications, permutations and variations will become apparent to those skilled in the art in light of the foregoing description.

What is claimed is:

1. A device for dispensing medication for medical treatment comprising a medication applicator having a cartridge, a nozzle removably attached to said cartridge, and an activator;

where the device dispenses one or more predetermined, preloaded doses of a medication for treatment of a migraine via the cartridge of said medication applicator when activated by the activator;

where the device is adapted to administer at least one dose of said medication while a user is in an upright position;

where a distal end of the nozzle of said device when inserted is adapted to be positioned in each nostril beyond an inferior turbinate prior to administering any dose of said medication;

the medication applicator having a safety interlock to prevent the dispensing of any of the one or more predetermined, preloaded medication doses until the safety interlock has been moved to a safety lock position that does not correspond to the selected medication dose of the one or more predetermined, preloaded medication doses being dispensed;

said safety interlock positioned in a second predetermined, preloaded medication dose position, wherein the second predetermined, preloaded medication dose position does not correspond to a first predetermined, preloaded dose of said medication;

wherein when the safety interlock is in the second predetermined, preloaded medication dose position said medication applicator is configured to allow activation to dispense the first predetermined, preloaded first dose of the medication;

said safety interlock positioned in a third predetermined, preloaded medication dose position, wherein the third predetermined, preloaded medication dose position does not correspond to a second predetermined, preloaded dose of said medication;

wherein when the safety interlock is in the third predetermined, preloaded medication dose position said medication applicator is configured to allow activation to dispense the second predetermined, preloaded second dose of the medication;

where the medication applicator is adapted to direct each dose of the medication into the nasal cavity adjacent to a sphenopalatine ganglion;

where the medication is dispensed as an aerosol mist.

2. The device for dispensing medication for medical treatment according to claim 1
where the medication applicator stores the medication and dispenses the medication as the aerosol mist;
where the medication applicator is adapted to dispense the medication through the nostril of the user.

3. The device for dispensing medication for medical treatment according to claim 1
where said nozzle of the medication applicator bends to form an angle of 5.0 to 60.0 degrees;
where the bend is located between an atomizer at a proximal end of the nozzle and the cartridge of the medication applicator.

4. The device for dispensing medication for medical treatment according to claim 3
where the nozzle comprises an insertion limiter;
where the insertion limiter is a flange located proximally on the nozzle and axially surrounding the nozzle;
where the insertion limiter limits the insertion distance of the nozzle into the nostril.

5. The device for dispensing medication for medical treatment according to claim 1
where the activator is adapted to dispense the one of the one or more predetermined, preloaded doses of the medication responsive to an action of the user;
where the activator comprises a plunger that is moved proximally by a spring;
where the plunger pushes a seal into the cartridge to dispense one dose of the medication;
where the plunger is adapted to move responsive to the action of the user.

6. The device for dispensing medication for medical treatment according to claim 5
where the action of the user comprises the activation of one or more buttons.

7. The device for dispensing medication for medical treatment according to claim 1
where the activator is operable to release the medication in two doses;
where a first dose is dispensed into a first nostril;
where a second dose is dispensed into a second nostril.

8. The device for dispensing medication for medical treatment according to claim 7
where the first dose of the medication is dispensed upon the activation of a first button;
where the second dose of the medication is dispensed upon the activation of a second button.

9. The device for dispensing medication for medical treatment according to claim 1
wherein the safety interlock is a three-position safety interlock;
where the three-position safety interlock prevents premature dispensing of the medication when placed in a safety lock position.

10. The device for dispensing medication for medical treatment according to claim 9
where the three-position safety interlock comprises a lock base that assumes one of three positions; where the three-position safety interlock prevents both the first predetermined, preloaded first dose of the medication and the second predetermined, preloaded second dose of the medication from being dispensed when the lock base is in a first safety lock position; where the three-position safety interlock permits the first predetermined, preloaded first dose of the medication to be dispensed and prevents the second predetermined, preloaded second dose of the medication from being dispensed when the lock base is in a second safety lock position; where the three-position safety interlock permits the second predetermined, preloaded second dose of the medication to be dispensed when the lock base is in a third safety lock position.

11. The device for dispensing medication for medical treatment according to claim 10
where the safety interlock prevents the lock base from moving to the third safety lock position until the first dose has been dispensed.

12. The device for dispensing medication for medical treatment according to claim 1
where the medication dispensed by the medication applicator is a 4% lidocaine solution.

13. A method of administering a medication for the treatment of a medical condition comprising:
inserting a nozzle of a device for dispensing medication for migraine treatment into a first nostril of a user while said user is physically oriented in an upright position such that a distal end of the nozzle is positioned beyond an inferior turbinate in a nasal cavity of the user prior to administering any dose of said medication;
unlocking an activator to dispense a first medication dose by moving a lock base of a safety interlock on the device for dispensing medication for migraine treatment from a first medication dose position to a second medication dose position;
activating the activator of said device for dispensing medication for migraine treatment, when the safety interlock is in the second medical dose position, to dispense said first medication dose of the medication as an aerosol mist directed through the nozzle into the nasal cavity adjacent to a sphenopalatine ganglion of said user;
inserting the nozzle of the device for dispensing medication for migraine treatment into a second nostril of said user such that the distal end of the nozzle is positioned beyond the inferior turbinate in the nasal cavity of the user prior to administering any dose of said medication;
unlocking the activator to dispense a second medication dose by moving the lock base of the safety interlock on the device for dispensing medication for migraine treatment from the second medication dose position to a third medication dose position; and activating the activator of said device for dispensing medication for migraine treatment, when the lock base of the safety interlock is in the third medical dose position, to dispense said second dose of the medication as the aerosol mist directed through the nozzle into the nasal cavity adjacent to the sphenopalatine ganglion of said user.

14. The method of administering a medication for the treatment of a medical condition according to claim 13 where the step of activating the activator to dispense the first dose comprises pressing a first button on the device for dispensing medication for medical treatment;

where the step of activating the activator to dispense the second dose comprises pressing a second button on the device for dispensing medication for medical treatment.

15. The device for dispensing medication for the treatment of a medical condition according to claim 13 further comprising:

where the safety interlock prevents the lock base from moving to the third medication dose position until the first dose has been dispensed.

* * * * *